United States Patent [19]
Youngs et al.

[11] Patent Number: 5,889,185
[45] Date of Patent: Mar. 30, 1999

[54] METHOD OF SYNTHESIZING ISOINDOLEQUINONES AND DERIVATIVES THEREOF

[75] Inventors: Wiley J. Youngs; Manisha Chakraborty, both of Akron, Ohio

[73] Assignee: The University of Akron, Akron, Ohio

[21] Appl. No.: 834,361

[22] Filed: Apr. 16, 1997

[51] Int. Cl.[6] .................................................. C07D 209/08
[52] U.S. Cl. .......................................... 548/470; 548/427
[58] Field of Search ...................... 548/470, 427

[56] References Cited

U.S. PATENT DOCUMENTS 4,494,547   1/1985   Myers ...................................... 128/659

OTHER PUBLICATIONS

"Umsezung von Rhodiumkomplexen mit Alkinolen und Alkinalen" by Müller and Dilger, *Chemiker Zeitung* (Germany), pp. 388–389, 1973.

"Novel Cyclization of Bis–(bromoacetyl)heteroaromatic Compounds. Synthesis of Heterocyclic Quinones" by Ghera et al., *J.C.S. Chem. Comm.,* pp. 134–135, 1974.

"Mono– und bis–heterokondensierte Dibenzothiophenchinone: Benzo–, Furo–, Thiopheno–, Selenopheno–, Telluropheno–, Pyrrolo–dibenzothiophenchinone" by Müller et al., *Chem. Ber. 108* (Germany), pp. 237–242, 1975.

"Synthese von Benzo–, Furano–, Thiopheno–, Selenopheno– und Pyrrolo–benzotriazolchinonen" by Müller and Winter, *Liebigs Ann. Chem.* (Germany), pp. 1876–1881, 1974.

"Synthese Substituierter Isobenzofuran–, Isobenzothiophen–, Isobenzoselenophen– und Isoindolo–4,7–Chinone" by Hambrecht et al., *Tetrahedron Letters No. 21,* pp. 1789–1790, 1976.

"Heterocycles by Cycloaddition. III. Dihydroisoindolequinone, the Correct Structure of the Proposed Azatetracyclononanedione" by Matsukubo and Kato, *Bulletin of the Chemical Society of Japan.* vol. 49, pp. 3333–3334, 1976.

"Synthesis of 2H–Isoindole–4,7–diones by 1,3–Dipolar Addition of Oxazolium 5–Oxides to 1,4–Quinones" by Myers et al., *J. Org. Chem.,* pp. 1202–1206,, 1980.

"Radiosensitization Studies on Mouse Sarcoma" by Infante et al. *Radiation Sensitizers,* pp. 497–501, 1980.

"Antimicrobial Metabolites of the Sponge Reniera sp." by Frincke and Faulkner, *J. Am. Chem. Soc.,* pp. 265–269, 1982.

"Conditions of Non–Stabilized Azomethine Ylides and Quinones Synthesis of the Reniera Isoindole" by Parker and Cohen, *Tetrahedron Letters,* vol. 25, No. 43, pp. 4917–4920, 1984.

*Naturally Occurring Quinones III: Recent Advances,* by R.H. Thomson, pp. 632–706, 1987.

"Redox–Controlled Bergman Cycloaromatizations. Designed Enediynes with DNA–Cleaving Properties and Antitumor Activity" by Nicolaou et al., *J. Am. Chem. Soc.,* pp. 9279–9282, 1992.

"Umsezung von Rhodiumkomplexen mit Alkinolen und Alkinalen" by Müller and Dilger, *Chemiker Zeitung* (Germany), pp. 388–389, 1973.

*Primary Examiner*—Joseph McKane
*Attorney, Agent, or Firm*—Renner, Kenner, Greive, Bobak, Taylor & Weber

[57] ABSTRACT

A method of synthesizing isoindolequinones comprising the step of reacting a 2,3-di(ethynyl)hydroquinone with a hydride selected from the group consisting of Group 15 and Group 16 hydrides, wherein said step of reacting takes place in an oxygen free environment.

10 Claims, No Drawings

METHOD OF SYNTHESIZING ISOINDOLEQUINONES AND DERIVATIVES THEREOF

This invention was made with government support under an agreement awarded by U.S. Department of Health and Human Services. The government may have certain rights to the invention.

TECHNICAL FIELD

This invention relates to the synthesis of isoindolequinones. More particularly, the present invention relates to a novel method for synthesizing isoindolequinones, from readily accessible starting materials, in a one-pot synthesis using environmentally benign solvents. Specifically, the method employs 2,3-di(ethynyl)hydroquinone and Group 15 and 16 hydrides as reactants.

BACKGROUND OF THE INVENTION

Isoindolequinones are known. Specifically, they are disclosed in U.S. Pat. No. 4,494,547 where they are generally defined according to the formula

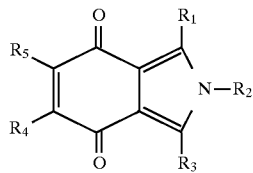

where $R_1$ and $R_3$ each separately is phenyl, substituted phenyl, alkyl of 1 to about 4 carbons, —CHO, —CH$_2$OR$_6$, —CO$_2$R$_6$, —COR$_6$, hydrogen, or together with $R_2$ is a divalent alkyl or alkenyl group of about 3 to about 5 carbons which form a cyclic ring; $R_2$ is phenyl, substituted phenyl, —CH$_2$OR$_6$, —CH$_2$CH$_2$OR$_6$, alkyl of 1 to about 4 carbons, or with either $R_1$ or $R_3$ is a divalent alkyl or alkenyl group of about 3 to about 5 carbons which form a cyclic ring; $R_4$ and $R_5$, which may be the same or different each separately is hydrogen, alkyl of 1 to about 4 carbons, —OR$_6$, —CO$_2$R$_6$, —COR$_6$, —CHO, —CH$_2$OR$_6$ or together $R_4$ and $R_5$ is a buradiene group which forms a benzene ring; $R_6$ is hydrogen or alkyl of 1 to about 4 carbons; provided that $R_1$ and $R_3$ are not both phenyl and that when $R_4$ and $R_5$ are both hydrogen, $R_1$, $R_2$ and $R_3$ are not all methyl.

Such compounds are important radiosensitizers that sensitize hypoxic cells to the lethal effect of radiation in cancer radiotherapy. These compounds are also known to have antibiotic activity.

Isoindolequinones were first synthesized by the treatment of rhodium heterocycles, prepared from diketodiynes and Wilkinson's catalysts, with nitrosobenzene. Cycloadditions of oxazolium 5-oxides with 1,4-benzoquinones also give isoindole derivatives. The first report of naturally occurring isoindole-quinone, 2,5-dimethyl-6-methoxyisoindole-4,7-quinone, isolated from the sponge Reniera, has been synthesized in moderate yields to form a pyrrole derivative by the cycloaddition of a yield to a quinone. Zinc-induced intramolecular cyclizations of bis-(bromoacetyl) heteroaromatic compounds also give isoindolequinones.

The synthesis of these compounds, however, is often inefficient inasmuch as a multi-step reaction is often required. Furthermore, the use of solvents that are deleterious to the environment are also often required.

Therefore there is a need in the art for a more efficient and simplistic method for synthesizing isoindolequinones.

SUMMARY OF INVENTION

It is, therefore, an object of the present invention to provide a method of synthesizing isoindolequinones.

It is another object of the present invention to provide a method of synthesizing isoindolequinones in a high yield reaction.

It is yet another object of the present invention to provide a method of synthesizing isoindolequinones in a one-pot synthesis.

It is still another object to provide a method of synthesizing isoindolequinones from readily available starting materials.

It is yet another object to provide a method of synthesizing isoindolequinones without the use of catalysts.

It is still yet a further object to provide a method of synthesizing isoindolequinones that provides for the easy isolation of the product.

It is another object to provide a method of synthesizing isoindolequinones employing environmentally benign and cost-effective solvents.

At least one or more of the foregoing objects, together with the advantages thereof over the known art relating to the synthesis of isoindolequinones, which shall become apparent from the specification that follows, are accomplished by the invention as hereinafter described and claimed.

In general the present invention provides a method of synthesizing isoindolequinones comprising the step of reacting a 2,3-di(ethynyl)hydroquinone with a hydride selected from the group consisting of Group 15 and Group 16 hydrides, wherein said step of reacting takes place in an oxygen free environment.

PREFERRED EMBODIMENT FOR CARRYING OUT THE INVENTION

The present invention provides a novel synthetic method for synthesizing isoindolequinones and derivatives thereof. Those of skill in the art understand that isoindolequinones may also be referred to as isoindolediones. These compounds are described in U.S. Pat. No. 4,494,547, which is incorporated herein by reference. Isoindolequinones are generally defined according to the formula I

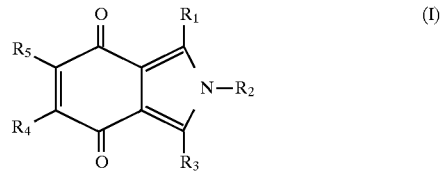

where $R_1$, $R_2$, $R_3$, $R_4$, and $R_5$ can be the same or different and are hydrogen or organic groups having between 1 and about 10 carbon atoms. Preferably, $R_1$ and $R_3$ each separately is phenyl, substituted phenyl, alkyl of 1 to about 4 carbons, —CHO, —CH$_2$OR$_6$, —CO$_2$R$_6$, —COR$_6$, hydrogen, or together with $R_2$ is a divalent alkyl or alkenyl group of about 3 to about 5 carbons which form a cyclic ring; $R_2$ is phenyl, substituted phenyl, —CH$_2$OR$_6$, —CH$_2$CH$_2$OR$_6$, alkyl of 1 to about 4 carbons or with either $R_1$ or $R_3$ is a divalent alkyl or alkenyl group of about 3 to about 5 carbons which form a cyclic ring; $R_4$ and $R_5$ which may be the same or different each separately is hydrogen, alkyl of 1 to about 4 carbons, —OR$_6$, —CO$_2$R$_6$, —COR$_6$, —CHO, —CH$_2$OR$_6$ or together $R_4$ and $R_5$ is a buradiene radical which forms a benzene ring; $R_6$ is hydrogen or alkyl of 1 to about 4 carbons; provided that $R_1$ and $R_3$ are not both phenyl and that when $R_4$ and $R_5$ are both hydrogen, $R_1$, $R_2$ and $R_3$ are not all methyl. Inasmuch as the above description does not include all possible derivations of isoindolequinones, the present invention should not be limited to the specific examples set forth above inasmuch as the present invention is believed to provide a method of synthesizing all synthetically achievable isoindolequinones.

Preferred are the isoindolequinone compounds wherein $R_1$ and $R_3$ are selected from phenyl alkyl of 1 to about 4 carbons and together with $R_2$, $R_1$ or $R_3$ forms a cyclic ring; $R_4$ and $R_5$ which may be the same or different are selected from hydrogen, alkyl of 1 to about 4 carbons, and methoxy. Preferred isoindole-quinone species include 2-alkyl-1,3,5,6-tetramethyl-isoindole-4,7quinone, isobenzofuran-quinone and isoindolequinone derivatives of Tris-(2-aminoethyl) amine.

In general, the synthetic method of the present invention includes reacting a 2,3-di(ethynyl)hydroquinone with a Group 15 or 16 hydride (IUPAC nomenclature). The reaction can be carried out at room temperature and atmospheric pressure. The reaction, however, should be carried out in the absence of oxygen, and preferably in an inert atmosphere.

The 2,3-di(ethynyl)hydroquinone can generally be represented by the formula II

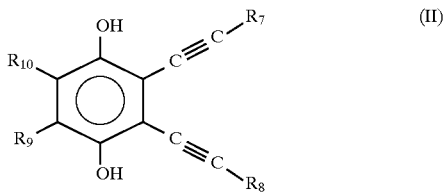

where $R_7$, $R_8$, $R_9$, and $R_{10}$ can be the same or different and include hydrogen or an organic groups having from 1 to about 10 carbon atoms. In a preferred embodiment, $R_9$ and $R_{10}$ are consistent with $R_4$ and $R_5$ above. Further, in a preferred embodiment, $R_7$ and $R_8$ will have from 1 to about 5 carbon atoms. For purposes of this disclosure, the 2,3-di(ethynyl)hydroquinones may generally be referred to as the quinone reactants.

The organic groups defined herein can contain unsaturation, but are preferably branched, straight-chain or cyclic alkyl groups. The organic groups can also include aromatic groups. It should be further understood that the organic groups can contain hetero atoms including oxygen, sulfur, silicon, phosphorus, and nitrogen. For example, the organic groups of the present invention include such organic groups as simple alkyl or alkenyl groups and their non-interfering oxygen, nitrogen, silicon and sulfur containing analogs. An example of one such group is a trimethylsilyl group. Although the preceding examples of possible organic groups have been recited, the scope of the invention should not be limited thereto.

The 2,3-di(ethynyl)hydroquinone reactants employed in the present invention can be prepared by coupling 2,3-diiodo-5,6-dimethylhydroquinone with trimethylsilylacetylene in the presence of a palladium-copper catalyst.

Those skilled in the art will be able to readily select Group 15 or 16 hydrides for the present method. Preferred hydrides include amines, phosphines and water. Most preferred are primary amines and water. For example, the primary amines can be selected from methyl amine, ethyl amine, propyl amine, or butyl amine. Other amines include Tris-(2-aminoethyl)amine phenyl amines, isopropyl amines and ammonium hydroxide. For purposes of this disclosure, the Group 15 and 16 hydrides may simply be referred to as hydrides.

Those skilled in the art will readily appreciate, without undue experimentation, the amount of reactant to be employed in the present invention. In most situations, a 1:1 molar ratio of reactants can be employed, with excess hydride or quinone reactant being used to drive the reaction. Typically, the less expensive or more readily available reactant will be added in excess.

The reaction can take place in any solvent system that will dissolve both the 2,3-di(ethynyl)hydroquinone and the hydride. It is preferred to employ a protic solvent, although aprotic solvents can be employed in a cosolvent system with a protic solvent. As those skilled in the art will appreciate, protic solvents include, but are not limited to methanol, ethanol, propanol, and isopropanol. Wet protic solvents can be employed, and it is preferred to employ dry protic solvents. The aprotic solvents that can be used within a cosolvent system with a protic solvent include toluene and tetrahydrofuran.

In a preferred embodiment, protic solvents can be mixed in 1:1 ratio; for example, a 1:1 blend of ethanol and methanol are employed. When a cosolvent system is employed, a 1:1 blend of protic to aprotic solvent can be used or, in some situations, a 3:1 blend of protic to aprotic can be employed.

It has been found that the use of degassed methanol gives greater yields; for example, 2,3-di(trimethysilyl)ethynyl 5,6-dimethylhydroquinone, when reacted with methyl, ethyl, propyl or butyl amine an degassed methanol gives an isoindolequinone with about 97% yield.

In one specific embodiment, 2-alkyl-1,3,5,6-tetramethylisoindole-4,7quinone, which is a substituted isoindolequinone, can be achieved in quantitative yields of greater than about 90% by the reaction of a 2,3-di(trimethysilyl)ethynyl 5,6-dimethylhydroquinone in methanol at room temperature under inert atmosphere. Yields of greater than 97% have also been observed.

In another embodiment Tris-(2-aminoethyl)amine (TREN) reacts with 2,3-di(trimethysilyl)ethynyl 5,6-dimethylhydroquinone in a solvent system including a 1:1 weight ratio of methanol: tetrahydrofuran (THF) to produce the isoindolequinone derivative of TREN.

In still another embodiment, 2-alkyl-1,3,5,6-tetramethylisoindole-4,7quinone can be achieved by the reaction of 2,3-diethynyl 5,6-dimethylhydroquinone using primary amines as both the reactant and the solvent. Specifically, these primary amines include those defined by the formula $NH_2R_a$ where $R_a$ includes organic groups having between 1 and about 10 carbon atoms, preferably between 1 and about 20 carbon atoms, and more preferably between 1 and about 10 carbon atoms. These carbon atoms can contain unsaturation, but are preferably branched, straight-chain, or cyclic alkyl groups. They can also contain aromatic groups. It should be further understood that the organic groups can contain hetero atoms including oxygen, sulfur and nitrogen. For example, the organic groups can include simple alkyl or alkenyl groups in their non-interfering oxygen, nitrogen and sulfur containing analogs.

Although it is preferred to employ reagents that provide high yield of product at room temperature, the scope of the present invention should not be limited thereto. Namely, some hydrides give better yields upon reflux.

For example, in one embodiment, yields greater than about 30% can be achieved when 2,3-diethynyl 5,6-dimethylhydroquinone is reacted with a secondary amine upon reflux. The secondary amine preferably includes two isopropyl organic groups, and it is most preferred to employ the secondary amine as the solvent system as well as the reactant. A cosolvent system of a protic and an aprotic solvent can also be employed.

In a similar situation, the 2,3-di(trimethysilyl)ethynyl 5,6-dimethylhydroquinone is refluxed with a molar equivalent of water in methanol to form isobenzofuran-quinone.

It should be further appreciated that the practice of the present invention will proceed, in most situations, without the use of a catalyst. The scope of the invention, however, should not be limited thereto inasmuch as the use of catalysts can improve the yield of the resultant product. Such improvement in yield is a function of the reactants employed, and those skilled in the art, without undue experimentation, will readily be able to determine those reactants that will more readily react in the presence of a catalyst. One particular catalyst that can be employed is $Pd(PPh_3)_2Cl_2$.

In order to demonstrate the practice of the present invention, the following isoindolequinones were synthesized. All product were characterized by $^1H$ and $^{13}C$ NMR, infrared, and mass spectroscopies and elemental analysis of carbon and hydrogen. The structure of the butyl derivatives of isoindolequinones was confirmed by X-ray crystallography. The examples set forth hereinbelow, however, are not to be viewed as limiting the disclosure. The claims will serve to define the scope of the invention.

GENERAL EXPERIMENTATION

All reactions were carried out using standard Schlenk techniques under an argon atmosphere unless otherwise specified. All the solvents and amines used in the reactions were degassed. Reaction temperatures were monitored externally. All reactions were monitored by thin-layer chromatography carried out on E. Merck silica gel plates (60F-254) using UV light. Flash column chromatography was carried out using silica gel (Bader: 40 μm). X-ray data was collected on a Syntex $P2_1$ diffractometer. Elemental analyses were done by Midwest Microlab in Indianapolis, Ind. and Schwarzkopf Microanalytical Laboratory in NY.

EXAMPLE 1

2,3-Di(trimethylsilyl)ethynyl 5,6dimethylhydroquinone (2)

To a degassed solution of 2,3-diiodo 5,6-dimethylhydroquinone (1)(3.6 g, 9.23 mmol), Pd"(PhCN)$_2$Cl$_2$ (176.9 mg, 0.46 mmol), PPh$_3$ (278.2 mg, 1.06 mmol), and CuI (297 mg, 1.56 mmol) in 110 mL to toluene under argon were added 2.5 mL (18.5 mmol) of diisopropylamine and 4.0 mL (28.6 mmol) of (trimethylsilyl)acetylene. After stirring at room temperature for a day the reaction mixture was opened to air, filtered and concentrated under vacuo. Flash column chromatography with 7% ethyl acetate in petroleum ether produced yellow compound (2) with 50.2% yield (1.53 g). Melting point 76°–77° C.

EXAMPLE 2

2,3-Diethynyl 5,6-dimethylhydroquinone (3)

To 2 (375 mg, 1.14 mmol), KF (198 mg, 3.4 mmol), 35 mL of methanol and 2.9 mL of water were added and stirred at room temperature for 1 h under air. The reaction was monitored by thin layer chromatography (tlc) every 10 mins after the first ½ h of the reaction. It was stopped by adding water as soon as starting material spot on tlc disappeared, otherwise the product was found to polymerize. The reaction mixture was then extracted with methylene chloride, washed thoroughly with water and dried over magnesium sulfate (MgSO$_4$). Flash column chromatography with 7% ethyl acetate in petroleum ether gave a creamy white product in 52.2% yield (111 mg). Melting point: gets darker after 133° C. and melts at 152° C.

EXAMPLE 3

General Procedure (A)

Synthesis of Isoindolequinones (4) using 2,3-Di(trimethylsilyl) ethynyl 1 5,6dimethylhydroquinone (2) and Methanol as Solvent Methanol was added to degassed 2 via syringe followed by 1.2–1.4 equivalents of amine under positive pressure of argon and stirred at room temperature for two days. After opening to air the solvent and trace of amine were removed under vacuo. Flash column chromatography of the residue gave pure yellow isoindolequinones in 97–98% yield.

EXAMPLE 4

2-Propyl-1,3,5,6-tetramethylisoindole-4,7-quinone, 4(R=Pr)

Following procedure A MeOH (0.8 mL) and propylamine (0.02 mL) were added to 2 (46.2 mg, 0.14 mmol) and stirred at room temperature for 2 days. Column chromatography with 3% ethyl acetate in petroleum ether gave pure yellow product in 97% yield (33.3 mg). Melting point 165°–167° C.

EXAMPLE 5

2-Butyl-1,3,5,6-tetramethylisoindole-4,7-quinone, 4 (R=Bu)

Procedure A was following using 2 (49.5 mg., 0.15 mmol), Butylamine (0.02 mL), and 2 mL of methanol. Column chromatography (3% ethyl acetate in petroleum ether) gave the butyl derivative in 98% yield (38.1 mg). Melting point 171°–172° C.

EXAMPLE 6

2-Phenyl-1,3,5,6-tetramethylisoindole-4,7-quinone, 4 (R=Ph)

The Phenyl derivative has been prepared as described in A, using (49.5 mg, 0.15 mmol), aniline (0.02 mL), and 2 mL of methanol by stirring at room temperature for 2 days. After opening to air methanol was removed under vacuo. The solid was washed with petroleum ether to remove trace excess of aniline. The residue after column chromatography was 3% ethyl acetate in petroleum ether produced phenyl derivative in 88% yield (36.8 mg). Melting point 212°–214° C.

EXAMPLE 7

2-Methyl-1,3,5,6-tetramethylisoindole-4,7-quinone, 4(R=Me)

2(M) solution of methylamine in methanol was used as received. To 2 (59.4 mg, 0.18 mmol), 2(M) solution of methylamine in methanol (9 mL) was added in large excess via syringe directly from Aldrich sure seal bottle under argon, and stirred for 2 days at room temperature. Using procedure A, the yellow product was isolated in 97% yield (37.9 mg). Melting point 212°–214° C.

EXAMPLE 8

2-Ethyl-1,3,5,6-tetramethylisoindole-4,7-quinone, 4 (R=Et)

Using procedure A, 2(M) solution of ethylamine in methanol (9 mL) was added in excess of 2 (59.4 mg, 0.18 mmol) from an Aldrich sure seal bottle via syringe. Column chromatography (3% ethyl acetate in petroleum ether) gave the yellow ethyl derivative in 98% yield (40.8 mg). Melting point 168° C.

EXAMPLE 9

1,3,5,6-Tetramethylisoindole-4,7-quinone, 4 (R=H)

General procedure A was followed using 2 (39.6 mg, 0.12 mmol), 2 mL of methanol saturated with ammonia (large excess). The mixture was stirred at room temperature for 12 h. Column chromatography (20% ethyl acetate in petroleum ether) gave yellow product in 88% yield (21.4 mg). Melting point: Turns black after 290° C. and becomes totally black until 360° C. without melting.

EXAMPLE 10

TREN derivative of 4 (5)

To a degassed solution of 2 (201.3 mg, 0.61 mmol) in methanol: THF (20 mL:20 mL) was added TREN 9tris(2-aminoethyl)amine (0.03 mL, 0.20 mmol, d=0.97) via syringe. The mixture was stirred at room temperature for 12 h, and refluxed for 24 h. After opening to air the solvent was removed in vacuo. Flash column chromatography (55% ethyl acetate in petroleum ether) gave the TREN-derivative of 4 in 57% yield (81.1 mg). melting point: melts with decomposition within 270°–278° C.

EXAMPLE 11

1,2,3,6-Tetramethyl-isobenzofuran-4,7-quinone (6)

To a degassed mixture of 2 (201.3 Mg, 0.61 mmol) 5 mL of water was added and the mixture was refluxed for a day. Removal of solvents and column chromatography of the residue with 1% ethyl acetate in petroleum ether gave 56% yield (69.6 mg) of the yellow product. Melting point 145°–147° C.

EXAMPLE 12

General Procedure (B): Synthesis of Isoindolequinones (4) using 2 or 2,3-Diethynyl-5,6-dimethylhydroquinone (3) and Amine as Solvent and Reactant A series of reactions were carried out using 2 or 3 and amines as reactants in excess. In some of the cases Rd catalyst was used. In a typical reaction in presence of catalyst, 2 or 3 was combined with 5% Pd"(PhCN)$_2$Cl$_2$, 12% PPh$_3$, excess amine, stirred at room temperature for a day, followed by refluxing for 8–12 h. Similar reactions without catalyst were carried out using amines as received. The yields of the products in these cases were moderate to good (40–78%). Only one reaction is reported here under this procedure.

EXAMPLE 13

2-Isopropyl-1,3,5,6-tetramethylisoindole-4,7-quinone, 4(R=iPr)

To a degassed mixture of 3 (50.2 mg, 0.27 mmol), Pd(PhCN)$_2$Cl$_2$ (4.0 mg, 0.01 mmol), and PPh$_3$ (10.4 mg, 0.04 mmol), isopropylamine (12 mL, distilled from BaO) was added and stirred overnight at room temperature following the general procedure B. Column chromatography (3% ethyl acetate in petroleum ether) gave the product in 49% yield (32.5 g). Melting point 166°–168° C.

EXAMPLE 14

Deuteration Study

Reaction of Butylamine and 2 in CD$_3$OD, 4(D$_6$)

An nmr tube was assembled with 2 (10 mg, 0.03 mmol), butylamine (0.01 mL) and 0.5 mL deuterated methanol (CD$_3$OD) in dry box. H nmr was monitored at room temperature every ½ h for the first 5 h and every 10 h after that. The peak at δ2.04 (due to the methyls on the quinone ring) remained unchanged but the peak at δ2.56 (corresponding to the methyls adjacent to the nitrogen) appeared as a small multiplet after 2 days. Integration showed 80% deuterated product containing D in the two methyls of the pyrrole ring distributed in 261 (1%), 262 (9%), 263 (28%), 264 (40%), 265 (22%) from FD-MS study.

Thus it should be evident that the synthetic method of the present invention are highly effective in producing isoindolequinones from readily synthesizable starting materials while employing one-pot conversions. The high yields obtained, and the ease of chromatographic isolation of the products, should be readily apparent. It should also be appreciated that the reaction requires no catalyst and uses environmentally benign solvents. The invention is particularly suited for the 2,3-di(ethynyl)hydroquinones disclosed herein, but is not necessarily limited thereto.

Based upon the foregoing disclosure, it should now be apparent that the use of the synthetic method described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, the substituant organic groups of the various reagents according to the present invention are not necessarily limited to those disclosed herein. Moreover, as noted hereinabove, other solvent systems can be employed. Thus, the scope of the invention shall include all modifications and variations that may fall within the scope of the attached claims.

What is claimed is:

1. A method of synthesizing isoindolequinones comprising the step of:

reacting a 2,3-di(ethynyl)hydroquinone with a hydride selected from the group consisting of Group 15 and Group 16 hydrides, wherein said step of reacting takes place in an oxygen free environment.

2. A method of synthesizing isoindolequinones as set forth in claim 1, wherein the 2,3-di(ethynyl)hydroquinone is defined according to the formula II

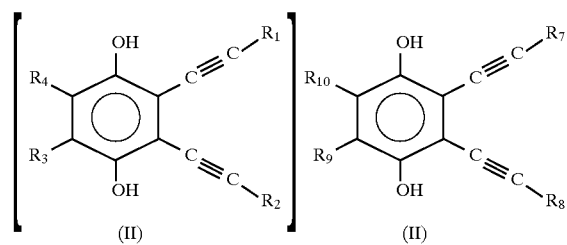

where $R_7$, $R_8$, $R_9$, and $R_{10}$ can be the same or different and include hydrogen or an organic group having up to about 10 carbon atoms.

3. A method of synthesizing isoindolequinones, as set forth in claim 2, wherein the 2,3-di(ethynyl)hydroquinone is 2,3-di(trimethylsilyl)ethynyl 5,6-dimethylhydroquinone.

4. A method of synthesizing isoindolequinones, as set forth in claim 2, wherein the 2,3-di(ethynyl)hydroquinone is 2,3-diethynyl 5,6-dimethylhydroquinone.

5. A method of synthesizing isoindolequinones, as set forth in claim 1, wherein the hydride is selected from the group consisting of amines, phosphines, and water.

6. A method of synthesizing isoindolequinones, as set forth in claim 5, wherein the hydride is a primary amine.

7. A method of synthesizing isoindolequinones, as set forth in claim 6, wherein the primary amine is defined according to the formula $NH_2R_a$, where $R_a$ is an organic group having from about 1 to about 30 carbon atoms.

8. A method of synthesizing isoindolequinones, as set forth in claim 7, wherein the primary amine is selected from the group consisting of methyl amine, ethyl amine, propyl amine, butyl amine, Tris-(2-aminoethyl)amine, phenyl amine, isopropyl amine, and ammonium hydroxide.

9. A method of synthesizing isoindolequinones, as set forth in claim 1, wherein said step of reacting takes place in a protic solvent.

10. A method of synthesizing isoindolequinones, as set forth in claim 2, wherein $R_7$ and $R_8$ include from 1 to about 5 carbon atoms.

* * * * *